United States Patent [19]

McGurk-Burleson et al.

[11] Patent Number: 4,867,157

[45] Date of Patent: * Sep. 19, 1989

[54] SURGICAL CUTTING INSTRUMENT

[75] Inventors: Erin McGurk-Burleson, San Clemente, Calif.; Elmer Koehler, St. Louis, Mo.; Victor Packham, Santa Ana, Calif.; James A. Thimsen; Terry L. Whipple, both of Richmond, Va.; Richard B. Caspari, Maidens, Va.

[73] Assignee: Baxter Travenol Laboratories, Inc., Deerfield, Ill.

[*] Notice: The portion of the term of this patent subsequent to Mar. 14, 2006 has been disclaimed.

[21] Appl. No.: 103,828

[22] Filed: Sep. 30, 1987

Related U.S. Application Data

[63] Continuation-in-part of Ser. No. 85,644, Aug. 13, 1987, Pat. No. 4,811,734.

[51] Int. Cl.$^4$ .............................................. A61B 17/32
[52] U.S. Cl. ..................................... 128/305; 30/29.5; 30/240
[58] Field of Search ............... 128/305, 312, 313, 318, 128/751, 755; 604/22; 30/264, 240, 29.5, 347

[56] References Cited

U.S. PATENT DOCUMENTS

| | | | |
|---|---|---|---|
| D. 219,252 | 11/1970 | Bogoff | D83/12 |
| D. 275,127 | 8/1984 | Edwards | D24/26 |
| 1,493,240 | 5/1924 | Bohn | |
| 2,532,370 | 12/1950 | Perrill | 30/29 |
| 2,729,210 | 1/1956 | Spencer | 128/2 |
| 3,308,828 | 3/1967 | Pippin | 128/310 |
| 3,618,611 | 11/1971 | Urban | 128/305 |
| 3,815,604 | 6/1974 | O'Malley et al. | 128/305 |
| 3,945,375 | 3/1976 | Banko | 128/6 |
| 3,973,222 | 2/1976 | Banko | 128/305 |
| 3,990,453 | 11/1976 | Douvas et al. | 128/305 |
| 4,014,342 | 3/1977 | Staub et al. | 128/305.1 |
| 4,099,529 | 7/1978 | Peyman | 128/305 |
| 4,111,207 | 9/1978 | Seiler, Jr. | 128/305 |
| 4,167,944 | 9/1979 | Banko | 128/305 |
| 4,203,444 | 5/1980 | Bonnell et al. | 128/276 |
| 4,274,414 | 6/1981 | Johnson et al. | 128/305 |
| 4,598,710 | 7/1986 | Kleinberg et al. | 128/318 |
| 4,603,694 | 8/1986 | Wheeler | 128/312 |
| 4,649,919 | 3/1987 | Thimsen et al. | 128/305 |

FOREIGN PATENT DOCUMENTS 452936 11/1948 Canada .

Primary Examiner—Andrew M. Dolinar
Attorney, Agent, or Firm—Gorgon L. Peterson; Frank J. Uxa, Jr.

[57] ABSTRACT

A surgical cutting instrument comprising an outer tube having a peripheral wall and a longitudinal axis. The outer tube has a plurality of openings arranged generally longitudinally along the outer tube. Each of the openings has first and second cutting edges defining portions of the periphery of such openings. An inner cutting member is rotatable within the outer tube. The inner cutting member has at least one cutting edge cooperable with the first and second cutting edges of the openings of the outer tube for cutting material from within the patient with a shearing action.

22 Claims, 3 Drawing Sheets

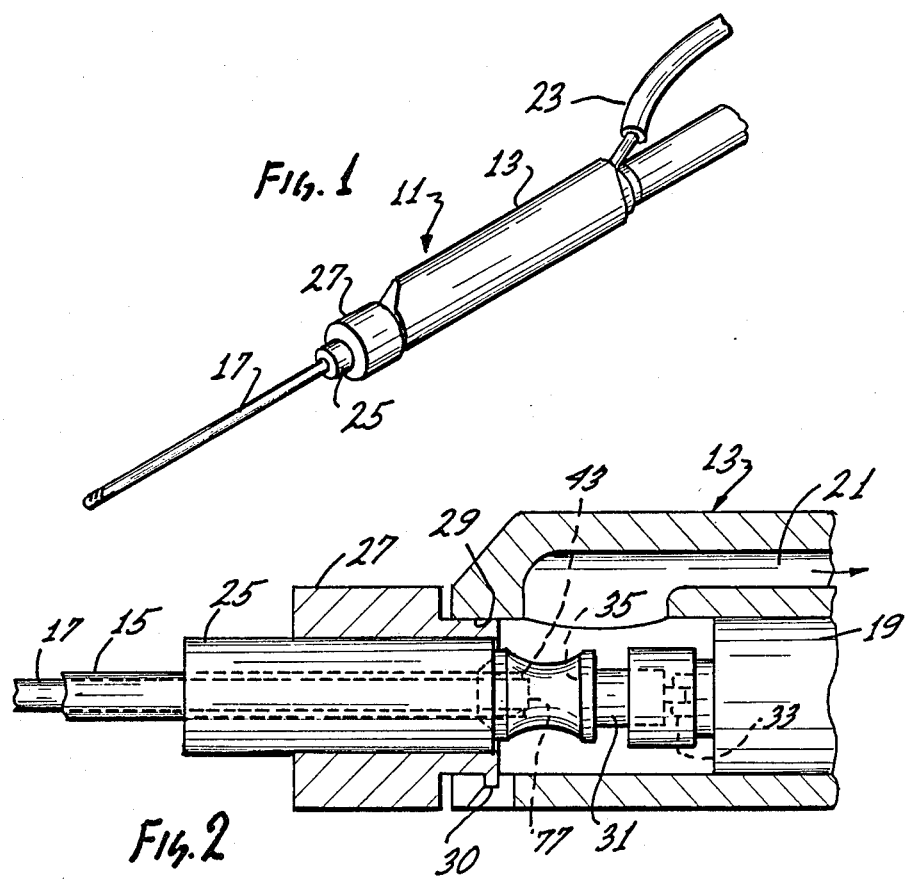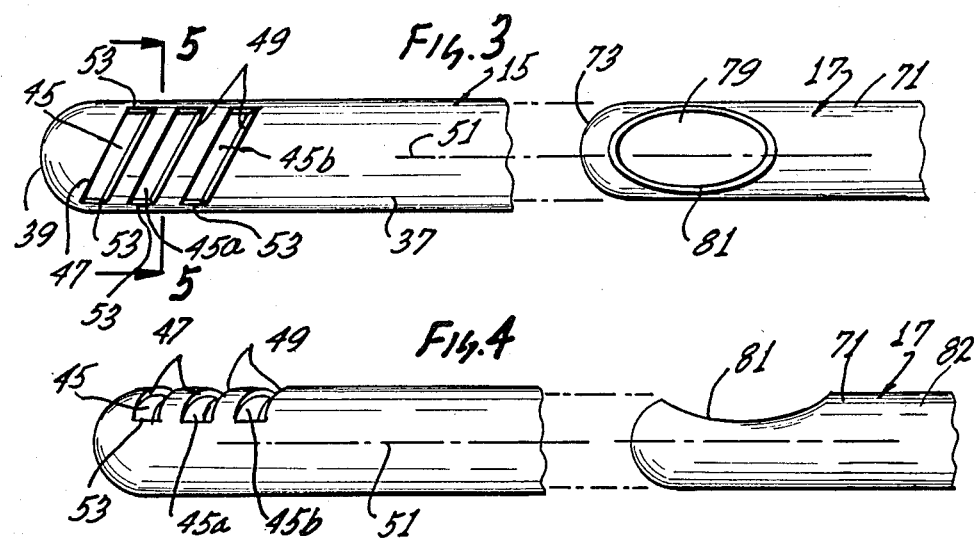

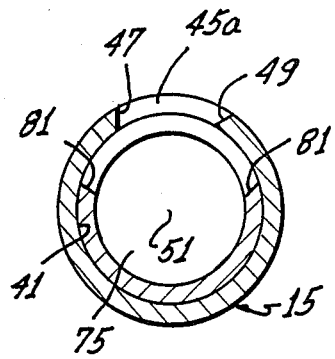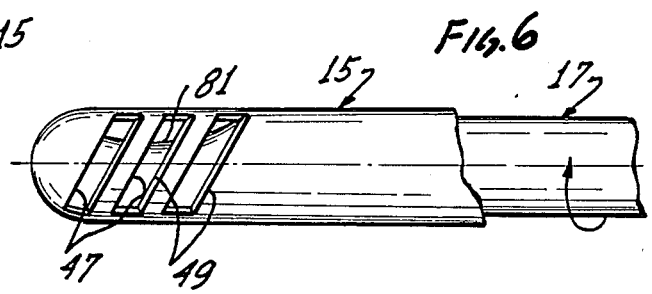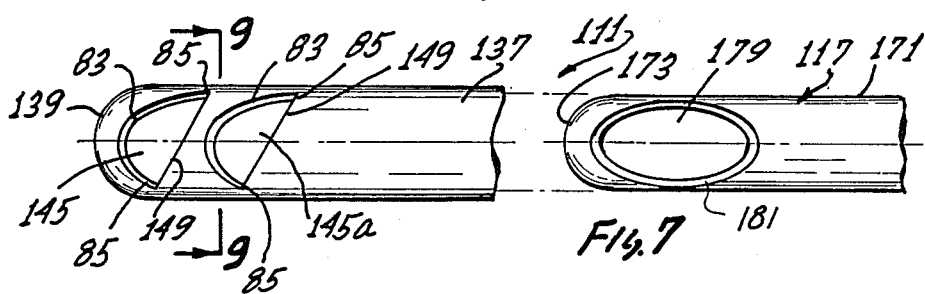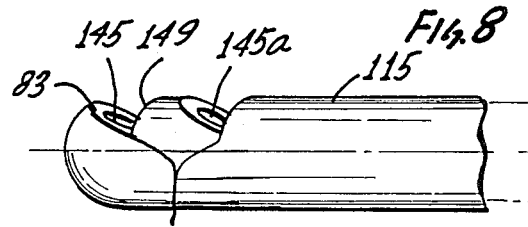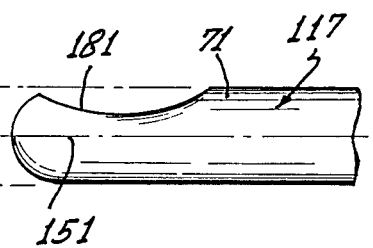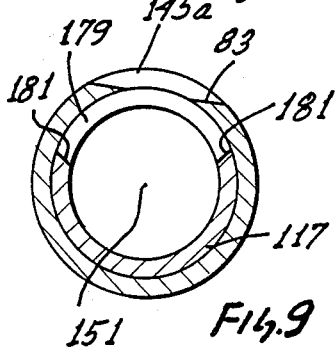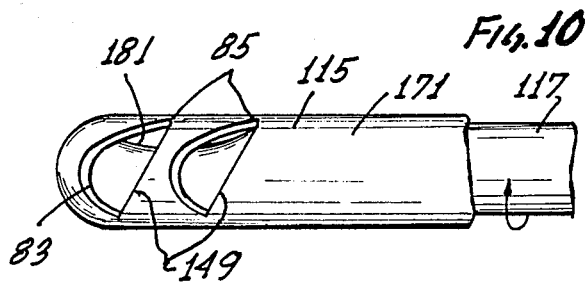

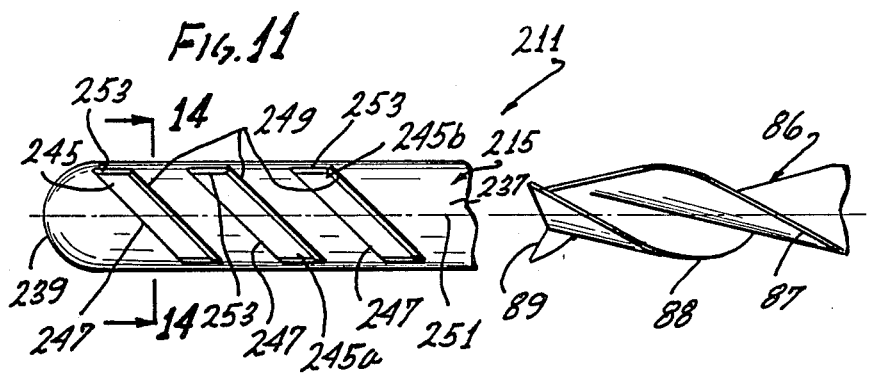
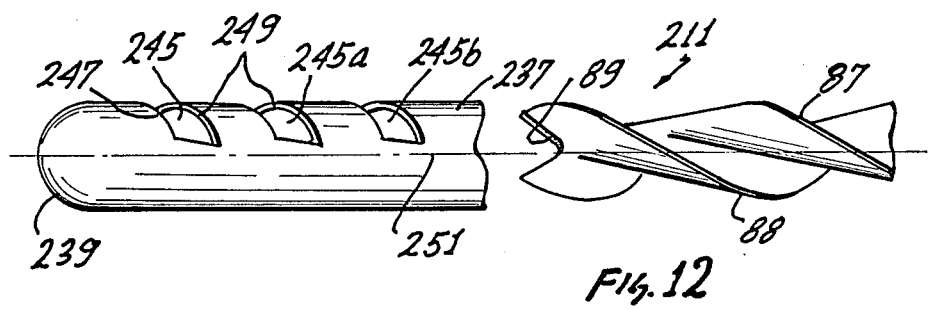
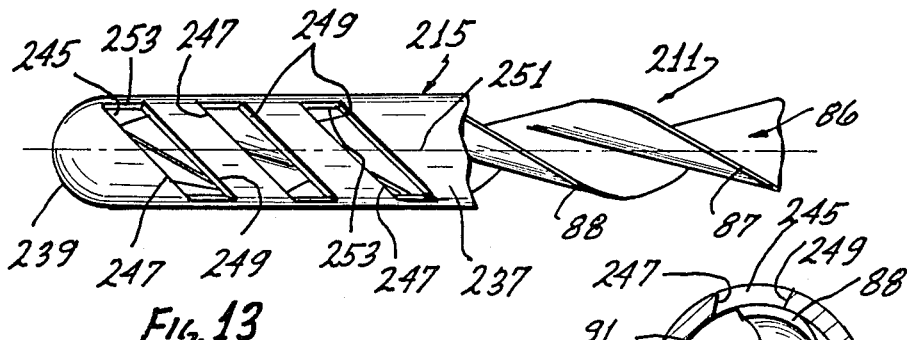
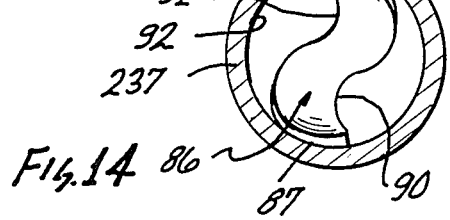

SURGICAL CUTTING INSTRUMENT

RELATED APPLICATION

This application is a continuation-in-part of copending application Ser. No. 085,644, filed Aug. 13, 1987, now U.S. Pat. No. 4,811,734.

BACKGROUND OF THE INVENTION

This invention relates to a surgical cutting instrument of the type employing rotary cutters. Instruments of this type are usable for various surgical procedures in various regions of the body, such as in the eye and knee. For example, the surgical cutting instruments may be inserted through a small opening into the knee joint and used for cutting the meniscus or other soft or hard material or tissue.

Generally, a surgical cutting instrument of this type includes an outer tube having a peripheral wall, an end wall, an opening in one or both of the peripheral wall and the end wall and a cutting edge defining at least a portion of the periphery of the opening. An inner cutting member, which may also be in the form of a tube, rotates or translates within the outer tube. The inner cutting member has a cutting edge that cooperates with the cutting edge of the outer tube for cutting material with a shearing action as the inner cutting member is moved relative to the outer tube. One surgical cutting instrument of this general type is shown and described in Johnson et al U.S. Pat. No. 4,274,414.

Another cutting instrument of this type is the whisker cutter. In this instrument, the outer tube has a plurality of small circular openings to adapt the instrument for cutting fine hair-like projections, such as synovial tissue, from within the knee. While the whisker construction is satisfactory for certain applications, it is not suitable for a broader range of applications. For example, the round edges of the circular small holes of the outer tube do not provide as good a scissors or shearing action as is desirable for some applications. In addition, the small holes also make the outer tube not particularly satisfactory for use as a curette.

Another type of inner cutter which has been suggested is a helical or auger cutter. For example, Banko U.S. Pat. No. 4,167,944 uses a helical cutter at the distal end of a device having a outer tube with a single circular opening. Staub, et al U.S. Pat. No. 4,014,342 uses an elongated helical cutter in conjunction with an outer tube having a single opening in the distal end thereof. Thimsen, et al U.S. Pat. No. 4,649,919 uses a helical cutter in combination with an outer sheath which is open at its distal end and proximally therefrom to form diametrically opposed tabs with inwardly extending lips. Pippin, U.S. Pat. No. 3,308,828 and Perrill U.S. Pat. No. 2,532,370 use helical cutters in conjunction with outer protective shields which do not have cutting edges or surfaces. These devices ten to become clogged with material removed from the patient's body, and/or are not effective or usable as a curette.

Notwithstanding a proliferation of known configurations for the outer tube and the inner cutting member, there are problems with poor cutting ability and inconsistent quality.

SUMMARY OF THE INVENTION

This invention provides a novel surgical cutting instrument having various different features which tend to solve the problems identified above. With this invention, the surgical cutting instrument is adapted for multiple applications, and the outer tube can serve a scraping function like a curette. In addition, cutting ability and quality are improved, and the likelihood of clogging is reduced.

According to one feature of the invention, the outer tube has a plurality of openings which provide multiple opportunities for cutting of material. However, the openings have at least one cutting edge and are substantially larger than the small-diameter circular openings of the whisker cutter. Consequently, this surgical cutting instrument can also serve like a curette in cutting and scraping tissue as the outer tube of the instrument is moved generally axially.

Each of the multiple openings preferably has first and second cutting edges defining portions of the periphery of each opening, more preferably with the first cutting edge being substantially straight as viewed in a particular direction perpendicular to the longitudinal axis of the outer tube. The use of an edge which is straight when viewed in this direction enhances the scissor-like or shearing action obtainable with the surgical cutting instrument. The shearing action can be further enhanced by having the first edge extend circumferentially of the outer tube at an acute angle relative to a radial plane. Of course, these features and characteristics can be employed in one or more of the openings. The openings may be substantially identical.

In a preferred construction, each of the substantially straight first cutting edges and the openings extend circumferentially of the outer tube for at least about 90 degrees. Each such straight edge may optionally define a proximal edge of the associated opening.

In one useful embodiment, the instrument includes a plurality of openings in the outer tube each of which has a distal edge and a parallel proximal edge, and each of which is oriented at an acute angle, preferably in the range of about 5 degrees to about 60 degrees, more preferably about 5 degrees to about 30 degrees, relative to a line perpendicular to the longitudinal axis of the outer tube. The distal edge and proximal edge of each opening are preferably oriented at substantially the same acute angle relative to the longitudinal axis of the outer tube. One or both of the distal edge and the proximal edge of each such opening includes a cutting edge. Further, in one embodiment both the distal edge and the proximal edge of such openings are preferably substantially straight as viewed in a particular direction perpendicular to the longitudinal axis of the outer tube. This feature provides the present instrument with substantial scrapping capability, enhancing the usefulness of the instrument as a curette.

According to one preferred embodiment, each of the openings in the outer tube includes a curved edge, which includes the second edge. The straight edge intersects the associated curved edge and substantially defines therewith the full periphery of the associated opening. The curved edge is preferably part oval as viewed in a direction perpendicular to the longitudinal axis of the outer tube.

In order to provide a sufficiently large opening so that the outer tube can better serve a curette-like function, the ratio of the length of the periphery of each opening to the outside diameter of the outer tube is at least about 1.5 to 1. If the ratio is less than this, use of the outer tube as a curette may be impaired. Although a ratio of over 1.5 to 1 is known for a single opening and for one of a multiplicity of openings, this ratio has not been employed heretofore for each of a plurality of longitudinally arranged openings. Preferably, to enhance the ability of the outer tube to serve as a curette, this ratio should be at least about 2 to 1, and for still improved results, the ratios can be in the range of 2.3 to 3.4 and greater to 1.

The ability of the outer tube to serve as a curette in response to axial motion can be enhanced by arranging the openings longitudinally on the outer tube and be lengthening the circumferential extent of the openings. In this regard, the openings preferably extend circumferentially of the outer tube for at least about 90 degrees to thereby lengthen the cutting edges in a direction generally transverse to the longitudinal axis of the outer tube.

In another preferred form of the invention, each of the second edges is also substantially straight as viewed in direction perpendicular to the longitudinal axis of the outer tube. The first and second edges can advantageously extend circumferentially, and the openings are preferably elongated circumferentially or in the direction of the first and second edges.

In one preferred construction, the first and second cutting edges intersect to form a corner, and the shearing action progresses along both of the cutting edges toward the corner. The corner tends to trap material to be cut and prevent its escape to thereby increase the cutting ability of the instrument and make the results more consistent. This feature may be present in one or more of the openings of the outer tube.

The inner cutting member can be tubular or non-tubular so long as it provides a cutting edge that cooperates with the cutting edges of the openings of the outer tube. In one embodiment, the inner cutting member preferably includes an inner tube having an opening therein, with the cutting edge of the inner tube extending along the periphery of the opening. Although the opening can be of various different configurations, one preferred configuration is oval because an oval opening can be used with a multiplicity of different opening configurations of the outer tube.

In another embodiment, the inner cutting member comprises a helical cutter blade, preferably such a blade which functions at least in part as an auger to aid in removing cut material from the cutting site, rotatable within the outer tube. The helical cutter blade has at least one cutting edge, preferably a plurality of, e.g., two, cutting edges, which cooperate with the cutting edge or edges of the openings in the outer tube for cutting material from within the patient with a shearing action that progresses along the cutting edge or edges of the openings as the helical cutter blade rotates. The helical cutter blade is preferably sized to fit in and in close spaced relation to the outer tube. This promotes the auger-like functioning of the helical cutter blade. Preferably, the helical cutter blade extends through a substantial portion of the length, more preferably through substantially the entire length, of the outer tube. The helical cutter blade includes at least one flute, and preferably a plurality of, e.g., two, flutes. These flutes or channels, which preferably run substantially the entire length of the helical cutter blade, act to aid in moving the cut material proximally of the cutting site. The helical cutter blade is preferably configured so that the lead angle of the helix is in the range of about 10 degrees to about 90 degrees, more preferably about 20 degrees to about 60 degrees and still more preferably about 30 degrees to about 45 degrees. The "lead angle" of the helix is defined as the angle of inclination of the helix from a plane that is perpendicular to the longitudinal axis of the helical cutter blade. Not only is the helical cutter blade effective, in combination with the cutting edge or edges associated with the outer tube, to cut material from the patient, but such blade is also very effective in removing such cut material from the cutting site without clogging the instrument. This is an important feature because, for example, it allows the instrument to be operated on a continuous basis while keeping the cutting edges free of cut material.

The inner cutting member is capable of being rotated relative to the outer tube, preferably at a rate of at least about 50 rpm, more preferably at a rate in the range of about 1000 rpm to about 5000 rpm.

The invention, together with additional features and advantages thereof, may best be understood by reference to the following description taken in connection with the accompanying illustrative drawings.

BRIEF DESCRIPTION OF THE DRAWINGS

FIG. 1 is an isometric view of a surgical cutting instrument constructed in accordance with the teachings of this invention.

FIG. 2 is an enlarged fragmentary sectional view illustrating the coupling of the outer tube and the inner cutting member to the handle.

FIG. 3 is a fragmentary, exploded top plan view of the distal regions of the inner and outer tubes.

FIG. 4 is a side elevational view of the construction shown in FIG. 3.

FIG. 5 is an enlarged sectional view taken generally along line 5—5 of FIG. 3.

FIG. 6 is a top plan view of the distal region of the surgical cutting instrument showing how the cutting edges cooperate to cut material.

FIG. 7 and 8 are top plan and side elevational views, respectively, similar to FIGS. 3 and 4, respectively, illustrating a second embodiment of the invention.

FIG. 9 is an enlarged sectional view taken generally along line 9—9 of FIG. 7, with the inner tube being fully inserted into the outer tube.

FIG. 10 is a top plan view of the distal region of the surgical cutting instrument showing how the cutting edges cooperate to cut material.

FIGS. 11 and 12 are top plan and side elevational views, respectively, similar to FIGS. 3 and 4, respectively, illustrating a third embodiment of the invention.

FIG. 13 is a top plan view of the distal region of the surgical cutting instrument shown in FIGS. 11 and 12 showing how the cutting edges cooperate to cut material.

FIG. 14 is an enlarged sectional view taken generally along line 14—14 of FIG. 11, with the helical cutter blade being fully inserted into the outer tube.

DESCRIPTION OF THE PREFERRED EMBODIMENTS

FIGS. 1–6 show a surgical cutting instrument 11 which generally comprises a handle 13, an outer tube 15, and an inner cutting member in the form of an inner tube 17. The inner tube 17 is receivable and rotatable within the outer tube 15. The outer tube 15 is fixedly attached to the handle 13 in a known manner. The handle 13 also provides a passage 21 which is coupled by a conduit 23 (FIG. 1) to a vacuum source (not shown) for applying suction pressure to the inner tube 17 to withdraw material severed during operation of the cutting instrument 11.

More specifically and by way of example, a sleeve 25 is suitably fixedly attached to the outer tube 15, and the sleeve in turn is releasably mounted on a collar 27 in a conventional manner, such as by ball detents and a key and key way (not shown). The collar 27 is removably received within a bore 29 of the handle 13 by a conventional quick disconnect connection 30. The inner tube 17 extends proximally of the sleeve 25 where it is coupled by a conventional coupling 31 to a drive shaft 33 (FIG. 2) of the motor 19. With this construction, the motor 19 can rotate the inner tube 17 within the outer tube 15 in a known manner. Vacuum pressure may be applied to the inner tube 17 via the passage 21 and a radial opening 35 in the coupling 31 in a conventional manner. The bearing support for the rotation of the inner tube 17 can be provided in whole or in part by the outer tube 15 or in any other suitable manner known in the art.

The outer tube 15 is sized for insertion through an opening, such as a puncture or incision, in a patient. For example, the outer tube 15 may be sized for insertion through an opening in the knee and may be used, for example, for cutting synovial tissue in the knee.

The outer tube 15 has a peripheral wall 37 and an end wall 39 at a distal end of the outer tube. Although various configurations are possible, the peripheral wall 37 is preferably cylindrical, and the end wall, in this embodiment, is preferably generally hemispherical and of the same radius as the peripheral wall. The outer tube 15 has a passage 41 (FIG. 5) which extends completely through the outer tube from a proximal end 43 (FIG. 2) all the way to the end wall 39 at the distal end of the outer tube. The passage 41 is cylindrical throughout the full length of the peripheral wall 37 and is hemispherical within the hemispherical end wall 39.

The outer tube 15 has openings 45, 45a and 45b. In one aspect, this invention differs from the prior art in that the outer tube 15 has multiple openings 45, 45a and 45b of a particular configuration and orientation and in the manner in which these openings cooperate with the helical cutter blade 17. Although the openings 45, 45a and 45b could be of different configurations, in this embodiment, the openings are substantially identical. The openings are arranged longitudinally along the outer tube 15 with the opening 45 being the most distal. The openings 45a and 45b lie entirely in the peripheral wall 37, and the opening 45 lies primarily in the peripheral wall and partially in the end wall 39.

Each of the openings 45-45b has axially spaced, cutting edges 47 and 49 defining substantial portions of the periphery of the associated opening. At least one of the edges 47 and 49 of each of the openings 45-45b and, preferably both of such edges, is substantially straight as viewed in a particular direction perpendicular to a longitudinal axis 51 of the outer tube 15. As shown in FIG. 3, this particular direction is a top plan view looking directly down on the openings 45-45b. The edges 47 and 49 of the opening 45 are parallel, and preferably all of these edges are parallel.

The edges 47 and 49 of each of the openings 45-45b are joined by relatively short, axial cutting edges 53. The cutting edges 47 form the distal edges of each of the associated openings 45-45b, and the cutting edges 49 form the proximal edges of such openings. The axial edges 53 are straight as viewed in FIG. 3, except that the lower (as viewed in FIG. 3) axial edge 53 of the opening 45 is curved slightly because of its presence in the hemispherical end wall 39. Except for the curvature of this one cutting edge 53, the openings 45-45b are completely identical, and the curvature of this one cutting edge 53 does not keep the openings 45-45b from being substantially or essentially identical.

At least one, and preferably both, of the cutting edges 47 and 49 of each of the openings 45-45b extend circumferentially of the outer tube 15 at an acute angle relative to a radial place as shown in FIG. 3. In addition, at least one, and preferably all, of the openings 45-45b extend circumferentially of the outer tube 15 for at least 90 degrees, and in this embodiment, the openings extend circumferentially for less than 180 degrees and about 160 degrees. This lengthens the cutting edges 47 and 49.

Each of the openings 45-45b is relatively large in area when compared with the usual small diameter circular whisker opening. Moreover, the ratio of the length of the periphery of each of the openings 45-45b to the outside diameter of the outer tube 15 in this embodiment is about 2.33 to 1. In the illustrated embodiment is about 2.33 to 1. The cutting edges 47, 49 and 53 maybe straight or beveled as desired. In the illustrated embodiment, the cutting edges 47 are straight as shown in FIG. 5, and the cutting edges 49 and 53 are beveled to slope downwardly as they extend inwardly when the outer tube 15 is oriented with the opening 45a facing directly upwardly. However, whether or not the cutting edges 47 and 49 are beveled, the sides of the openings 45-45b defined by the cutting edges 47 and 49 are parallel as viewed in FIG. 3.

Although the inner tube 17 can be of various different constructions, in this embodiment, it includes a cylindrical, peripheral wall 71 and a hemispherical end wall 73 at the distal end of the inner tube. The inner tube 17 has a passage 75 which extends from a proximal end 77 (FIG. 2) of the inner tube all the way to the end wall 73.

The inner tube 17 has an opening 79 and a cutting edge 81 extending along the periphery of the opening 79 and completely circumscribing the opening. The cutting edge 81 can be of any configuration that will appropriately cooperate with the cutting edges 47, 49 and 53 to shear material to be cut in a scissors-like fashion while crowding such material generally toward one of the axial cutting edges 53. In this embodiment, the opening 79 and the cutting edge 81 are generally oval, and more specifically, are generally elliptical as shown in FIG. 3. As shown in FIG. 4, the cutting edge 81 and, therefore, the opening 79 are in both the peripheral wall 71 and the end wall 73. The cutting edge 81 appears elliptical as viewed in FIG. 3 and forms an arc as shown in FIG. 4 which lies entirely above a central longitudinal axis 82 of the inner tube 17.

The opening 79 can be of various other configurations, including a configuration which matches the configuration of the openings 45-45b of the outer tube 15. If desired, an appropriate cutting edge may be provided on a non-tubular rotatable member, such as a helix (e.g., as shown in FIGS. 11 to 14), in lieu of on the inner tube 17.

In use of the cutting instrument 11, it is inserted through an opening in the knee to a region, such as the synovial tissue, which is to be cut, and the motor 19 is energized to begin unidirectional rotation of the inner tube 17 within the outer tube 15. This moves the cutting edge 81 along the cutting edges 47 and 49 of each of the openings 45-45b as generally illustrated in FIG. 6 to provide shearing of scissors-like cutting along all of the cutting edges 47 and 49 while crowding material toward the short axial cutting edges 53. This provides a reliable and effective cutting of the material along the cutting edges 47 and 49 in a way that consistency and cutting efficiency are enhanced. However, the cutting action along the cutting edges of the openings 45-45b is out of phase i.e., the cutting edge 81 at any one instant is in a different relative position with respect to each opening 45-45b as shown in FIG. 6. Because the openings 45-45b are symmetrical about the axis 51, the inner tube 17 can be rotated in either direction within the outer tube 15, and the same desirable cutting action is achieved. In addition, the outer tube 15 may be moved longitudinally such that the edges 47 and 49 provide a curetting-type of action for cutting and scraping material. The cutting edges 47 are particularly effective in providing this curetting-type of action. Suction is applied through the passage 21 and the opening 35 and the passage 75 of the inner tube 17 so as to remove the cut or severed material after it is cut so that the cutting instrument need not be withdrawn from the incision to accomplish this.

FIGS. 7-10 show a cutting instrument 111 which is identical to the cutting instrument 11 in all respects not shown or described herein. Portions of the cutting instrument 111 corresponding to portions of the cutting instrument 11 are designated by reference characters increased by 100 over those employed for the cutting instrument 11.

The primary difference between the cutting instruments 11 and 111 is in the configuration of the openings 145 and 145a. Each of the openings 145 and 145a is identical, and in this embodiment, the opening 45b is eliminated. The openings 145 and 145a have parallel cutting edges 149 of the same length, orientation and configuration as the cutting edges 49, except that the cutting edges 149 in this embodiment, are not beveled. Thus, the cutting edges 149 are straight as viewed in a particular direction, i.e., a top plan view (FIG. 7) looking straight down on the openings 145 and 145a.

Each of the openings 145 and 145a also has a curved cutting edge 83 which is part oval as viewed in FIG. 7 and which intersects the opposite ends of the associated cutting edge 149 to form corners 85. Accordingly, the cutting edges 83 and 149 define the full periphery of the associated openings 145 and 145a. The opening 145a is located entirely in the peripheral wall 137, and the opening 145 is located primarily in the peripheral wall and partly in the end wall 139.

Each of the openings 145 and 145a may be visualized as formed by intersecting planes which intersect on one side of the axis 151 to form the cutting edges 83 and 149. These cutting planes enter the outer tube 115 from such one side, and the intersection of the planes form the corners 85. In actual practice, the openings 145 and 145a may be formed by rotating cutting tools (not shown), and thus reference herein to formation of the openings with planes is only for purposes of visualization of the opening geometry and does not refer to the process of cutting the openings or to whether or not the edges may be beveled.

The openings 145 and 145a may have the same circumferential extent as the openings 45-45b. In the embodiment of FIGS. 7-10, the ratio of the length of the periphery of each of the openings 145-145a to the outside diameter of the outer tube 115 is about 3.38 to 1.

The operation of the cutting instrument 111 is essentially as described above for the cutting instrument 11. In this regard, the shearing or scissors action proceeds along the cutting edges 83 and 149 toward the corners 85 by virtue of the cooperation between the cutting edges 83 and 149 and the cutting edge 181. The material being cut tends to be trapped in the corner 85 and is prevented from escaping. The shearing action terminates essentially simultaneously along the cutting edges 83 and 149 at the corner 85 of the opening 145; whereas, with the opening 145a, the shearing action along the cutting edge 149 is complete slightly before the completion of the shearing action along the cutting edge 83.

FIGS. 11-14 show a cutting instrument 211 which is identical to the cutting instrument 11 in all respects not shown or described herein. Portions of the cutting instrument 211 corresponding to portions of the cutting instrument 11 are designated by reference characters increased by 200 over those employed for the cutting instrument 11.

One primary difference between the cutting instruments 11 and 211 is in the use of a helical cutter blade 86 rather than the inner tube 17. Although the helical cutter blade 86 can be of various different constructions, in this embodiment, it includes mutually opposing cutting edges 87 and 88 and a generally fish tail shaped end 89 at the distal end of the helical cutter blade 86. The cutting edges 87 and 88 can be of any configuration that will appropriately cooperate with the cutting edges 249 and 253 to shear material to be cut in a scissors-like fashion while crowding such material generally toward one of the axial cutting edges 253. As shown, the cutting edges 87 and 88 extend substantially the entire length of helical cutter blade 86. However, these cutting edges may be extended only so far as needed to effectively cooperate with the cutting edges of openings 245-245b. Thus, the edges of helical cutter blade 86 proximally of this effective cutting region need not be cutting edges. Helical cutter blade 86 includes two flutes or channels 90 and 91 which run substantially the entire length of helical cutter blade 86. Helical cutter blade 86 has a lead angle of 40 degrees. Helical cutter blade 86 fits within the inner wall 92 of outer tube 215.

Another primary difference between the cutting instruments 11 and 211 is in the configuration and orientation of the openings 245, 245a and 245b. Each of the openings 245-245b is identical. Each of the openings 245-245b have parallel edges 247 and 249 and axial edges 253. Each of the openings 245-245b is oriented at an angle of 10 degrees relative to a line perpendicular to the longitudinal axis 251 of outer tube 215. That is, each of the axial edges 253 is oriented at an angle of 10 degrees relative to the longitudinal axis of outer tube 215. Put another way, each of the parallel edges 247 and 249 is oriented at an angle of 10 degrees relative to a line perpendicular to the longitudinal axis 251 of outer tube 215. This feature provides beveling to edges 249, and may enhance the usefulness of cutting instrument 211 as a curette while allowing openings 245-145b to be easily and precisely positioned in outer tube 215.

Each of the edges 247, 249 and 253 is straight as viewed in a particular direction, i.e., viewing cutting instrument 211 from the top at a 10 degree angle from the vertical. The openings 245a and 245b are located entirely in the peripheral wall 237, and the opening 245 is located primarily in the peripheral wall and partly in the end wall 239.

The openings 245-245b may have the same circumferential extent as the openings 45-45b.

Each of the individual features of each embodiment shown in the drawings may be substituted for a corresponding feature in any of the other illustrated embodiments. For example, the helical cutter blade 86 may be used in place of the inner tubes 17 and 117, and the angularly oriented openings 245-245b may be used in place of the openings 45-45b.

In use of the cutting instrument 211, it is inserted through an opening in the knee to a region, such as the synovial tissue, which is to be cut, and the motor in energized to begin unidirectional rotation of the helical cutter blade 86 within the outer tube 15. This moves the cutter edges 87 and 88 along the cutting edge 249 of each of the openings 245-245b as generally illustrated in FIG. 13 to provide shearing of scissors-like cutting along all of the cutting edges 249 while crowding material toward the short axial cutting edges 253, each of which is shown in FIG. 13 as the top end of one of the openings 245-245b. This provides a reliable and effective cutting of the material along the cutting edges 249 in a way that consistency and cutting efficiency are enhanced. The auger-like action of the helical cutter blade 86 aids in transporting the cut material proximally from the cutting site, thus reducing clogging of the instrument by the cut material. The cutting action along the cutting edges of the openings 245-245b is out of phase i.e., the cutting edges 87 and 88 at any one instant are in a different relative position with respect to each opening 245-245b as shown in FIG. 13. In addition, the outer tube 215 may be moved longitudinally such that the edges 247 and 249 provide a curetting-type of action for cutting and scraping material. Edges 247 are particularly effective in providing this curetting-type of action. Suction is applied to cutting instrument 211, in much the same way is in applied to cutting instrument 11, so as to remove the cut or severed material after it is cut so that the cutting instrument 211 need not be withdrawn from the incision to accomplish this.

Although exemplary embodiments of the invention have been shown and described, many changes, modifications and substitutions may be made by one having ordinary skill in the art without necessarily departing from the spirit and scope of this invention.

What is claimed is:
1. A surgical cutting instrument comprising:
   an outer tube sized for insertion through an opening in a patient, said outer tube having a generally cylindrical peripheral wall and an outside diameter;
   said outer tube having a plurality of openings arranged generally longitudinally along the outer tube including distal and proximal openings;
   each of said openings having a cutting edge defining at least a portion of the periphery of such opening;
   the ratio of the length of the periphery of each of said openings to said diameter of the outer tube is at least 1.5 to 1;
   an inner cutting member rotatable within said outer tube; and
   said inner cutting member having a cutting edge cooperable with said cutting edges of the openings of the outer tube for cutting material from within the patient with a shearing action that progresses along both said cutting edges as the inner cutting member rotates.

2. An instrument as defined in claim 1 wherein the ratio of the length of each of said peripheries of said openings to said diameter is about 2 to 1.

3. An instrument as defined in claim 1 wherein said cutting edge of one of said opening extends circumferentially of said outer tube at an angle relative to a radial plane.

4. An instrument as defined in claim 1 wherein each of said openings extends circumferentially of the outer tube for at least about 90 degrees.

5. An instrument as defined in claim 1 wherein said inner cutting member includes an inner tube rotatable within said outer tube and having an opening therein, and said cutting edge of said inner tube extends along the periphery of the opening in the inner tube.

6. An instrument as defined in claim 1 wherein said opening in said inner tube is generally oval.

7. An instrument as defined in claim 1 including a handle, a motor carried by the handle, means for mounting the outer tube on the handle and means for coupling the inner cutting member to the motor so that the motor can rotate the inner cutting member.

8. An instrument as defined in claim 1 wherein the cutting edge of each of said openings includes first and second cutting edges which intersect to form a corner and said shearing action progresses along both of the first and second cutting edges of all of said openings toward the associated corner.

9. An instrument as defined in claim 8 wherein the outer tube has a longitudinal axis and a first of said openings is formed at least in part by first and second planes which intersect on one side of said axis and form the first and second cutting edges, respectively, of the first opening, said first plane and said second plane enter the outer tube from said one side and the intersection of said planes forms said corner.

10. An instrument as defined in claim 1 wherein said inner cutting member is a helical cutter blade.

11. A surgical cutting instrument comprising;
   an outer tube sized for insertion through an opening in a patient, said outer tube having a peripheral wall and a longitudinal axis;
   said outer tube having a plurality of openings arranged generally longitudinally along the outer tube including distal and proximal openings, each of said openings extending circumferentially for at least about 90 degrees;
   each of said openings having a cutting edge defining at least a portion of the periphery of such opening;
   an inner cutting member rotatable within said outer tube; and
   said inner cutting member having a cutting edge cooperable with said cutting edges of said openings of the outer tube for cutting material from within the patient with a shearing action that progresses along said cutting edges of said openings as the inner cutting member rotates.

12. An instrument as defined in claim 11 wherein a portion of each of said cutting edges of said openings extends circumferentially of said outer tube at an acute angle relative to a radial plane.

13. A surgical cutting instrument comprising:
   an outer tube sized for insertion through an opening in a patient, said outer tube having a peripheral wall and a longitudinal axis, said outer tube having a plurality of openings arranged generally longitudinally along said outer tube, each of said openings having first and second cutting edges defining portions of the periphery of such openings;
   a helical cutter blade extending within said outer tube and being rotatable within said outer tube, said helical cutter blade having at least one cutting edge cooperable with said first and second cutting edges of said openings of said outer tube for cutting material from within the patient with a shearing action that progresses along said first and second cutting edges as said helical cutter blade rotates;

each of said openings having a distal edge and a parallel proximal edge each of which is oriented at an acute angle relative to a line perpendicular to said longitudinal axis of said outer tube; and said distal edges and said proximal edges of all of said openings being substantially straight as viewed in a particular direction perpendicular to said longitudinal axis of said outer tube and are positioned at substantially the same acute angle relative to said longitudinal axis of said outer tube.

14. An instrument as defined in claim 13 wherein each of said first opening extends circumferentially of the outer tube for at least about 90 degrees.

15. An instrument as defined in claim 13 wherein the peripheral wall of said outer tube is generally cylindrical and has an outside diameter and the ratio of the length of the periphery of each of said openings to said diameter is at least about 1.5 to 1.

16. An instrument as defined in claim 13 wherein said openings are substantially identical.

17. An instrument as defined in claim 13 wherein each of said first edges of said openings defines the proximal edge of the associated opening.

18. An instrument as defined in claim 13 wherein said acute angle is in the range of about 5 degrees to about 60 degrees.

19. An instrument as defined in claim 13 wherein said openings are substantially identical, the peripheral wall of said outer tube is generally cylindrical and has an outside diameter and the ratio of the length of each of said peripheries of said openings to said diameter is about 2 to 1.

20. An instrument as defined in claim 13 including a handle, a motor carried by said handle, means for mounting said outer tube on said handle and means for coupling said helical cutter blade to said motor so that said motor can rotate said helical cutter blade.

21. An instrument as defined in claim 13 wherein said helical cutter blade extends through a substantial portion of the length of said outer tube.

22. An instrument as defined in claim 13 wherein said helical cutter blade extends through substantially the entire length of said outer tube.

* * * * *

UNITED STATES PATENT AND TRADEMARK OFFICE
CERTIFICATE OF CORRECTION

PATENT NO. : 4,867,157
DATED : September 19, 1989
INVENTOR(S) : Erin McGurk-Burleson et al It is certified that error appears in the above—identified patent and that said Letters Patent is hereby corrected as shown below:

```
Column 1, line 57 change "ten" to -- tend --.
Column 3, line 10 change "be" to -- by --.
Column 3, line 19 before "direction" insert -- a --.
Column 6, line 10 change "place" to -- plane --.
Column 6, line 21-line 22 delete "In the illustrated
embodiment is about 2.33 to 1.".
Column 6, line 22 change "maybe" to -- may be --.
Column 7, line 27 change "lll" to -- 11 --.
Column 8, line 58 change "245-145b" to -- 245-245b --.
Column 9, line 10 change "in energized" to -- is energized --.
Column 9, line 36 change "is in applied" to
-- it is applied --.
Column 10, line 2 change "opening" to -- openings --.
```

Signed and Sealed this

Twenty-eighth Day of July, 1992

Attest:

DOUGLAS B. COMER

Attesting Officer    Acting Commissioner of Patents and Trademarks